United States Patent [19]

van den Brink et al.

[11] Patent Number: 4,552,636

[45] Date of Patent: Nov. 12, 1985

[54] PROCESS FOR REMOVING AMMONIUM-IONS IN AN OXIME PREPARATION FROM A HYDROXYL-AMMONIUM SALT

[75] Inventors: Franciscus van den Brink, Geldrop; Marinus Alfenaar, Schinnen, both of Netherlands

[73] Assignee: Stamicarbon B.V., Geleen, Netherlands

[21] Appl. No.: 616,681

[22] Filed: Jun. 4, 1984

[30] Foreign Application Priority Data

Jun. 10, 1983 [NL] Netherlands .................... 8302072

[51] Int. Cl.⁴ .................... B01D 13/02; C07C 131/00
[52] U.S. Cl. .................... 204/182.4; 564/259
[58] Field of Search .................... 204/180 P, 301; 564/259

[56] References Cited

U.S. PATENT DOCUMENTS

| | | | |
|---|---|---|---|
| 3,641,150 | 2/1972 | De Rooij | 564/259 |
| 3,701,809 | 10/1972 | De Rooij et al. | 423/392 |
| 3,766,038 | 10/1973 | Beck et al. | 204/180 P |
| 4,253,928 | 3/1981 | Blytas et al. | 204/180 P |

Primary Examiner—Andrew H. Metz
Assistant Examiner—B. J. Boggs, Jr.
Attorney, Agent, or Firm—Cushman, Darby & Cushman

[57] ABSTRACT

A process for the preparation of a hydroxylammonium slat and an oxime from said hydroxylammonium salt and an aldehyde or keton is disclosed in which an aqueous acid reaction medium is kept in circulation between a zone for the synthesis of the salt and a zone for the synthesis of the oxime and in which nitrate ions and/or nitrogen monoxide are continuously supplied as a reducible nitrogen source for the liquid kept in circulation, wherein the circulation liquid is subjected to an electrodialysis to remove the ammonium ions formed as a byproduct in the hydroxylammonium salt synthesis.

4 Claims, 2 Drawing Figures

PROCESS FOR REMOVING AMMONIUM-IONS IN AN OXIME PREPARATION FROM A HYDROXYL-AMMONIUM SALT

The invention relates to a process for the preparation of a hydroxylammonium salt and an oxime from said hydroxylammonium salt and an aldehyde or ketone in which an aqueous acid reaction medium is kept in circulation between a zone for the synthesis of a hydroxylammonium salt and a zone for the synthesis of an oxime from said hydroxylammonium salt and in which nitrate ions or nitrogen monoxide are supplied continuously as a reducible nitrogen source to the liquid kept in circulation, and ammonium ions formed as byproducts in the reduction of the nitrogen source are removed.

Such a process, in which nitrate ions are used as a reducible nitrogen source, is known from the U.S. Pat. No. 3,701,809. The use of nitrogen monoxide in such a process is known from the U.S. Pat. No. 3,641,150. The contents of these patent specifications are hereby incorprated by reference.

The removal of $NH_4{}^+$ ions from the reaction medium is important to keep the pH of the reaction medium between the limits required for the process. The disadvantage of the process according to the said patent specifications lies in the manner in which $NH_4{}^{30}$ is removed. According to that state of the art, $NH_4{}^+$ is removed as $N_2$ by applying Piria's equation:

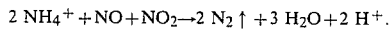

$$2\ NH_4{}^+ + NO + NO_2 \rightarrow 2\ N_2 \uparrow + 3\ H_2O + 2\ H^+.$$

However, in this process for the $NH_4{}^+$ removal, the nitrogen oxides used also oxidize the low concentrations of organic products present in the circulating liquid, in which process nitro and nitroso compounds and other oxidation products are formed. These products poison the noble metal catalyst in the hydroxylammonium salt synthesis zone.

Moreover, in Piria's reaction equation, ½ mole NO and ½ mole $NO_2$ are used per mole $NH_4{}^+$ to be removed. This total amount of 1 mole nitrogen oxides has been formed by the oxidation of 1 mole $NH_3$ so that for the removal of 1 mole $NH_4{}^+$ also 1 additional mole $NH_3$ will be required.

The total nitrogen loss expressed in moles $NH_3$ per mole $NH_4{}^+$ removed is consequently 2 moles. The object of the invention is to eliminate the said disadvantages. The improvement according to the invention is characterized in that the circulating liquid containing ammonium ions is subjected to an electrodialysis in which, on the diluate side of the electrodialysis membrane, ammonium ions are withdrawn from the aqueous acid reaction medium, and on the concentrate side, the concentration of ammonium is increased.

Thus the formation of organic oxidation products that poison the catalyst is avoided. The nitrogen balance is more favourable because no $NH_3$ disappears as $N_2$.

Figure 1:
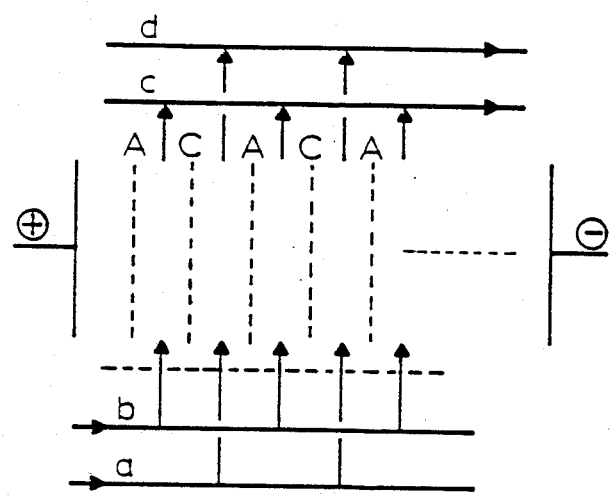
FIG. 1 represents the ED arrangement of the invention.

In the process of the invention an $NH_4{}^+$-containing aqueous acid reaction medium, from the preparation of a hydroxylammonium salt and an oxime, is transported after the oxime synthesis zone to an electrodialysis (ED) arrangement (as shown in FIG. 1) as incoming diluate flow (line b) and after the ED treatment as discharging diluate flow (line c) to the hydroxylammonium salt synthesis zone.

The concentrate flow is formed by a separate flow (incoming flow, line a, discharging flow line d) that can be recirculated (in FIG. 1 between d and a) and which can be drained to prevent too high a concentration of $NH_4{}^+$.

The principle of the ED arrangement as applied according to the invention is represented in FIG. 1. The two liquid flows, called diluate and concentrate, are passed between anion- and cation-exchanging membranes (A resp. C) while a current passes through these membranes. The diluate in this case is the aqueous acid reaction medium containing the $NH_4{}^+$ ions that are to be removed. In FIG. 1 lines a and b represent respectively the incoming concentrate and diluate flows. Lines c and d represent respectively the discharging-/diluate, and concentrate flows. In the process according to the invention the $NH_4{}^+$ ions of the incoming diluate flow b find their way into the discharging concentrate flow d. The result of the electrodialysis is that the concentrate is concentrated and the diluate diluted with $NH_4{}^+$-ions.

The degree to which a certain ion contributes to the total transport of charges (ion transport) is determined by its concentration in the two electrolyte flows and its mobility in the membrane. A membrane in which different ions have different mobilities is perm-selective: if the concentrations are equal, the more mobile ion will be separated selectively from the less mobil one. Thus C and A are perm-selective: the mobility of anions resp. cations, except protons, is zero in the membranes. A C-membrane, for instance, may also be permselective for different cations if their mobilities differ. The first form of permselectivity is determined by the nature of the ion-exchanging groups in the membrane, the second mainly by charge, size, solvation, etc. of the ions. Furthermore, in addition to the transport under the influence of the electric field (migration), transport under the influence of differences in concentration, i.e. diffusion, will also take place.

Important in the reaction medium are, in the first instance, $NH_4{}^+$, $H^+$ and, if the acid used in the reaction medium is phosphoric acid, $H_2PO_4{}^-$.

It has now been found that the mobility of the phosphate ion through the A-membrane is much lower than that of the $NH_4{}^+$ ion through the C-membrane on the one side and that of the $H^+$ through the A-membrane on the other (an A-membrane is not permselective for $H^+$) so that $NH_4{}^+$ can be removed selectively.

In a practical embodiment the chosen acid concentration on the concentrate side will be higher than on the diluate side. The resulting diffusion will prevent a loss of acid from the diluate to the concentrate.

The electrodialysis can be effected continuously as well as batchwise. The temperature limits of the liquids during the electrodialysis are determined by the temperature which the ED membranes can bear. Important also is the linear velocity of the liquid. This can be varied from 0.4–2 cm.sec$^{-1}$. Preference is given to a velocity of 0.5–1.2 cm.sec$^{-1}$. The chosen current density may be between 100 and 1000 A.m$^{-2}$.

The above is further elucidated in the following non-limiting examples.

EXAMPLE I

The electrodialysis is effected under the following experimental conditions.

The ED apparatus is a Selemion DU-06 stack of Asahi Glass with 9 cells. The effective surface per cell is 209 cm$^2$. The anode consists of platinum on titanium, the cathode used is the stainless steel cathode SS (SUS-27) that is a standard accessory to the apparatus. The membranes used are Selemion AMV, as an A-membrane, and Selemion CMV, as a C-membrane. The temperature of the liquid in the apparatus is about 35° C. The linear throughput rate of the circulating liquid is 0.8 cm.sec$^{-1}$. For the purpose of effecting an undisturbed osmosis a minimum difference in pressure between concentrate and diluate, up to 6.5 mbar, is maintained.

2 liters diluate composed of 2.8 moles.kg$^{-1}$ H$_3$PO$_4$ and 0.8 mole.kg$^{-1}$ NH$_4^+$ and 2 liters concentrate with the same composition are subjected to ED at a current density of 250 A.m$^{-2}$.

Figure 2:
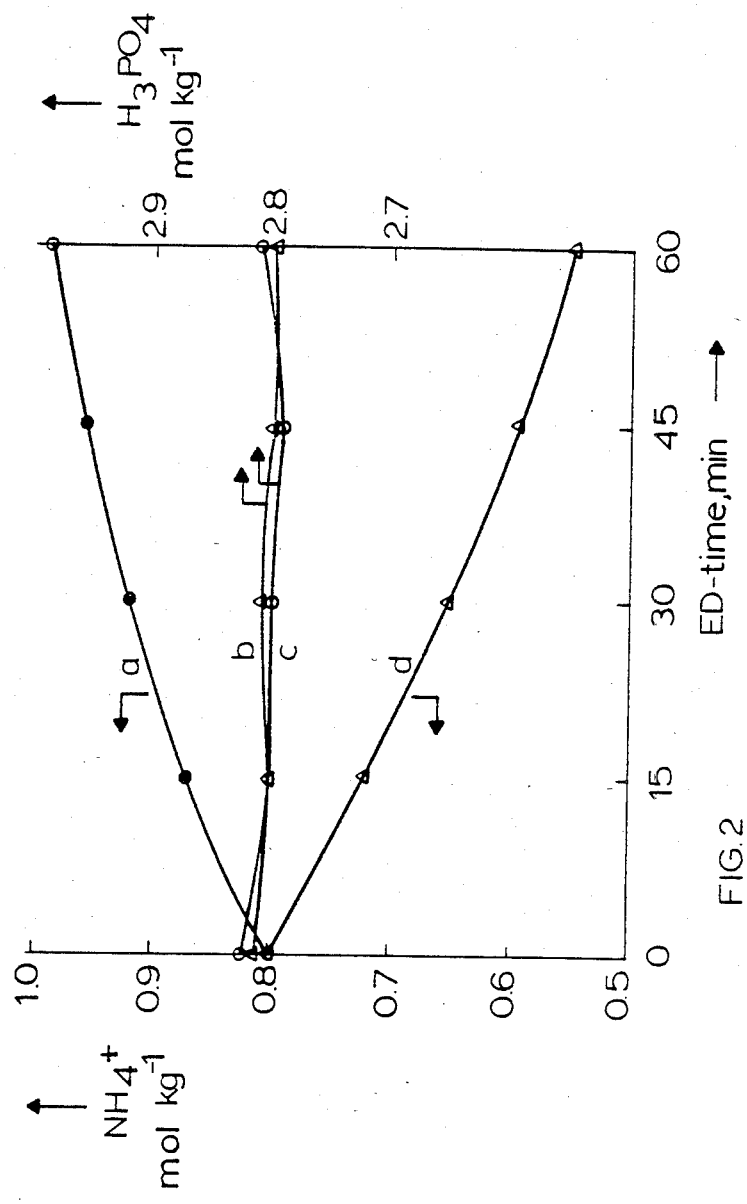
FIG. 2 is a graph that shows that as the ED time increases, a decrease of the $NH_4{}^+$ concentration takes place in the diluate and an increase thereof in the concentrate.

The results of this experiment are shown in FIG. 2. In this figure, line a relates to NH$_4^+$ concentration in the concentrate flow and line d to the NH$_4^+$ concentration in the diluate flow. Lines b and c related to the H$_3$PO$_4$ concentration in the diluate and concentrate flows respectively. FIG. 2 shows that, if the ED time increases, a decrease of the NH$_4^+$ concentration takes place in the diluate and an increase thereof in the concentrate. The phosphoric acid concentrations in the diluate as well as in the concentrate hardly change. Consequently, there is a selective transport of NH$_4^+$ ions from diluate to concentrate.

EXAMPLE II

Under the same conditions as in example I an electrodialysis is carried out in which the NH$_4^+$ concentration in the concentrate flow is 0.42 mole.kg$^{-1}$ and in the diluate flow 0.33 mole.kg$^{-1}$. The phosphoric acid concentrations in the two flows are both 3.75 moles.kg$^{-1}$ and the current density was 500 A.m$^{-2}$. Under these conditions a mole flux of NH$_4^+$ from diluate to concentrate of 0.12 mmole.sec$^{-1}$ is found. This example shows that by means of electrodialysis it is possible to transport NH$_4^+$ ions from a less concentrated diluate flow to a more concentrated concentrate flow.

EXAMPLES III EN IV

Under the same conditions as in example I, with a current density of 250 A.m$^{-2}$, the effect of the phosphoric acid concentration is examined. In example III this is higher in the concentrate flow than in the diluate flow (3.61 moles.kg$^{-1}$ in concentrate and 3.54 moles.kg$^{-1}$ in diluate), in example IV the situation is reversed (3.56 moles.kg$^{-1}$ in concentrate and 3.66 moles.kg$^{-1}$ in diluate). The NH$_4^+$-concentration in the concentrate flow is 0.19 mole.kg$^{-1}$ (example III) and 0.28 mole.kg$^{-1}$ (example IV) and in the diluate flow 0.43 mole.kg$^{-1}$ (example III) and 0.41 mole.kg$^{-1}$ (example IV).

In both examples 0.13 mmole NH$_4^+$.sec$^{-1}$ is transported from diluate to concentrate. In example III the transport of phosphoric acid is 0.27 mmole.sec$^{-1}$ from concentrate to diluate and in example IV 0.05 mole.sec$^{-1}$ from diluate to concentrate. This shows that the NH$_4^+$ transport is determined mainly by migration, whereas the transport of phosphoric acid is influenced very strongly by diffusion. This diffusion can be utilized to prevent loss of phosphoric acid from the diluate flow by using in the concentrate flow a higher phosphoric acid concentration than in the diluate flow.

What is claimed is:

1. A process for preparing a hydroxylammonium salt and an oxime comprising:
   conducting a synthesis of a hydroxylammonium salt in a first reaction zone;
   synthesizing an oxime from said hydroxylammonium salt and an aldehyde or ketone in a second reaction zone;
   circulating an aqueous acid reaction medium between the hydroxylammonium synthesis zone and the oxime synthesis zone wherein a reducable nitrogen source in the form of nitrate ions or nitrogen monoxide is continuously supplied to said circulating rection medium being fed to the first reaction zone whereby ammonium, ion by-products are formed during the reduction of the nitrogen source in said first reaction zone;
   subjecting the reaction medium from the second reaction zone to an electrodialysis treatment with an electrodialysis membrane, wherein a first diluate flow composed of said reaction medium passes along one side of said electrodialysis membrane and a discharge concentrate flow passes along the other side of said electrodialysis membrane whereby ammonium ions pass from said first diluate flow through said membrane into said discharge concentrate flow.

2. A process according to claim 1 wherein the acid concentration in the concentrate flow is higher than the acid concentration in the diluate flow.

3. A process according to claim 1, wherein the linear velocity of the circulating liquid is controlled between 0.5 and 1.2 cm.sec$^{-1}$.

4. A process according to claim 1, wherein the current density is between 100 and 1000 A.m$^{-2}$.

* * * * *